(12) United States Patent
Moseley et al.

(10) Patent No.: US 12,035,953 B1
(45) Date of Patent: Jul. 16, 2024

(54) BONY FUSION IMPLANT, INSERTION INSTRUMENT, AND METHODS

(71) Applicant: Spinal Simplicity, LLC, Overland Park, KS (US)

(72) Inventors: Todd Moseley, Olathe, KS (US); Luke Luallin, Fairway, KS (US); Adam Rogers, Olathe, KS (US); Christian Aragonez, Kansas City, MO (US); Jeff Slover, Lee's Summit, MO (US); Tony Hartlage, Prospect, KY (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 18/504,480

(22) Filed: Nov. 8, 2023

(51) Int. Cl.
*A61B 17/86* (2006.01)
*A61B 17/70* (2006.01)
*A61F 2/30* (2006.01)
*A61F 2/44* (2006.01)
*A61L 27/44* (2006.01)

(52) U.S. Cl.
CPC ........ *A61B 17/864* (2013.01); *A61B 17/7055* (2013.01); *A61F 2/30988* (2013.01); *A61F 2/4455* (2013.01); *A61L 27/44* (2013.01); *A61F 2002/30995* (2013.01)

(58) Field of Classification Search
CPC .............................. A61B 17/864; A61L 27/44
See application file for complete search history.

(56) References Cited

U.S. PATENT DOCUMENTS

| | | | |
|---|---|---|---|
| 6,517,542 B1* | 2/2003 | Papay | A61C 8/0022 606/232 |
| 2010/0152575 A1* | 6/2010 | Henderson | A61B 17/7055 606/279 |
| 2011/0137352 A1* | 6/2011 | Biedermann | A61B 17/8635 606/305 |
| 2011/0137354 A1* | 6/2011 | Biedermann | A61B 17/8883 606/312 |
| 2013/0110183 A1* | 5/2013 | Duggal | A61B 17/809 606/328 |
| 2015/0057711 A1* | 2/2015 | Kim | A61N 1/05 606/304 |
| 2018/0116814 A1* | 5/2018 | Sullivan | A61B 17/8645 |
| 2019/0262048 A1* | 8/2019 | Sutika | A61B 17/864 |

FOREIGN PATENT DOCUMENTS

WO   2023137124 A2   7/2023

* cited by examiner

*Primary Examiner* — Christian A Sevilla
(74) *Attorney, Agent, or Firm* — Erise IP, P.A.

(57) ABSTRACT

Systems, methods, and devices for bony fusion are disclosed. A threaded cannulated implant may be inserted into a target space, such as in the sacroiliac joint. The implant may have a distal section, a proximal section, and a central section between the distal section and the proximal section. The distal section may comprise cutting threads and flutes for self-drilling the implant into bone. The proximal section may be configured to couple to an insertion instrument for the implant. The central section may have a lattice structure through which bone graft may flow to promote bone ingrowth. A solid core region may be located inwards from the lattice structure. The central section may also have openings through the core region to connect the lattice structure to the cannula.

20 Claims, 8 Drawing Sheets

BONY FUSION IMPLANT, INSERTION INSTRUMENT, AND METHODS

CROSS-REFERENCE TO RELATED APPLICATIONS

This non-provisional patent application shares certain common subject matter with U.S. Application Ser. No. 18/504,635, filed Nov. 8, 2023, and entitled "SYSTEMS, METHODS, AND DEVICES FOR LATERAL AND POSTERIOR SACROILIAC JOINT FUSION." The above-identified application is hereby incorporated by reference in its entirety.

TECHNICAL FIELD

Embodiments of the present disclosure generally relate to systems, devices, and methods for bony fusion. More specifically, embodiments of the present disclosure relate to implants having an open architecture for fusion and stabilization of bones and insertion instruments and methods therefor.

RELATED ART

The spine consists of a column of twenty-four vertebrae that extends from the skull to the hips. The most inferior lumbar vertebra (L5) connects to the sacrum, which is a large bone that is formed by the fusion of the sacral vertebrae. On each side of the sacrum is an ilium, and the sacrum articulates with each ilium to form two sacroiliac (SI) joints. The SI joints play a significant role in absorbing impact from walking, lifting, and other movements.

When the ligaments or bony surfaces are damaged (e.g., due to trauma, arthritis, or other conditions), the SI joints can be a source of intense pain that can radiate into the leg. Inflammation in the SI joints is known as sacroiliitis. Sacroiliitis can be treated via non-surgical and surgical methods. Sacroiliitis may be treated surgically via an SI joint fusion procedure that uses an implant device to provide stability. Typical posterior SI joint implants are not made out of metal, leading to lower strength, and are deficient in promoting bone ingrowth. Additionally, posterior SI implants commonly are wedge shaped and are impacted into the SI joint and have a risk of working their way back out of the SI joint. Implants with improved control of insertion and that mitigate back out are needed. Other regions of the body may require the use of a bone screw for stabilization of bone, such as the foot, ankle, craniomaxillofacial, or the like. Improvements in bony fusion devices are needed.

SUMMARY

In some embodiments, the techniques described herein relate to an implant for bony fusion at a target space, including: a plurality of external threads extending along a length of the implant; a cannula extending along a longitudinal axis of the implant; a distal section; a proximal section configured to be coupled to an insertion instrument; and a central section between the proximal section and the distal section, the central section including: an interior core region adjacent to the cannula; a lattice structure located laterally between the interior core region and a minor diameter of the plurality of external threads; and a plurality of openings extending through the interior core region, the plurality of openings connecting the lattice structure to the cannula.

In some embodiments, the techniques described herein relate to an implant, wherein the implant is configured to be packed with bone graft, and wherein the plurality of openings is connected to the lattice structure such that the bone graft flows between the plurality of openings and the lattice structure.

In some embodiments, the techniques described herein relate to an implant, wherein the distal section includes at least one cutting flute for self-drilling the implant into the target space.

In some embodiments, the techniques described herein relate to an implant, wherein the proximal section includes internal threading for threadedly engaging the insertion instrument, wherein rotation of the insertion instrument rotates the implant for insertion into the target space.

In some embodiments, the techniques described herein relate to an implant, wherein at least a portion of the plurality of external threads includes at least one thread heel configured to reduce proximal movement of the implant when inserted into the target space.

In some embodiments, the techniques described herein relate to an implant, wherein the at least one thread heel is oriented in a first direction to prevent interference with threading of the implant during insertion.

In some embodiments, the techniques described herein relate to an implant, wherein the central section includes a length of about 30% to about 60% of the length of the implant.

In some embodiments, the techniques described herein relate to an implant, wherein the implant is formed from at least one of: a titanium alloy, stainless steel, magnesium, a polymer, a bioresorbable material, or an allograft, and wherein the implant is coated with hydroxyapatite.

In some embodiments, the techniques described herein relate to an implant for bony fusion of a target space, including: a cannula along a longitudinal axis of the implant; a distal section configured to self-drill the implant into bone; a proximal section; and a central section between the distal section and the proximal section, including: a lattice structure fluidly connected to the cannula, wherein the lattice structure is configured to receive bone graft for bone ingrowth of the implant, wherein the implant includes a plurality of external threads extending along a length of the implant.

In some embodiments, the techniques described herein relate to an implant, wherein the central section further includes: a core region adjacent to the cannula, and a plurality of fenestrations extending through the core region to fluidly connect the cannula to the lattice structure.

In some embodiments, the techniques described herein relate to an implant, wherein the lattice structure extends laterally from a perimeter of the core region to a minor diameter of the plurality of external threads.

In some embodiments, the techniques described herein relate to an implant, wherein the plurality of fenestrations follows a thread path of the plurality of external threads.

In some embodiments, the techniques described herein relate to an implant, wherein the implant includes a variable diameter that increases from the distal section to the proximal section.

In some embodiments, the techniques described herein relate to an implant, wherein the target space is a sacroiliac joint, and wherein the plurality of external threads of the implant is configured to embed into a sacrum and an ilium of the sacroiliac joint.

In some embodiments, the techniques described herein relate to an implant, wherein the implant is configured to be inserted into the sacroiliac joint via a posterior approach.

In some embodiments, the techniques described herein relate to an implant, wherein the proximal section includes a plurality of internal threads and a plurality of recesses configured for coupling to an insertion instrument.

In some embodiments, the techniques described herein relate to a method for bony fusion of a target space, including: providing an implant having a cannula along a longitudinal axis, including: a plurality of external threads extending along a length of the implant; a distal section; a proximal section configured to be coupled to an insertion instrument; and a central section between the proximal section and the distal section, the central section including: an interior core region adjacent to the cannula; a lattice structure located laterally between the interior core region and a minor diameter of the plurality of external threads; and a plurality of openings extending through the interior core region, the plurality of openings connecting the lattice structure to the cannula; and providing instructions, the instructions including steps of: couple the implant to the insertion instrument; and insert the implant into the target space using the insertion instrument.

In some embodiments, the techniques described herein relate to a method, wherein the instructions further include: make a minimally invasive incision; successively insert a series of dilators into the minimally invasive incision to create a working channel; and dock into the target space using a final dilator, the final dilator including at least one distal tang to engage with the target space.

In some embodiments, the techniques described herein relate to a method, wherein the distal section includes cutting threads and flutes configured to self-drill the implant into the target space.

In some embodiments, the techniques described herein relate to a method, wherein the instructions further include: pack the implant with bone graft, wherein the bone graft flows from between the cannula, the plurality of openings, and the lattice structure.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current present disclosure will be apparent from the following detailed description of the embodiments and the accompanying drawing figures.

BRIEF DESCRIPTION OF THE FIGURES

Embodiments of the present disclosure are described in detail below with reference to the attached drawing figures, wherein.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The subject matter of the present disclosure is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claims. Terms should not be interpreted as implying any particular ordering of various steps described unless the order of individual steps is explicitly described.

The following detailed description of embodiments of the present disclosure references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized and changes can be made without departing from the scope of the present disclosure. The following detailed description is, therefore, not to be taken in a limiting sense. The scope of embodiments of the present disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Overview

Figure 1:
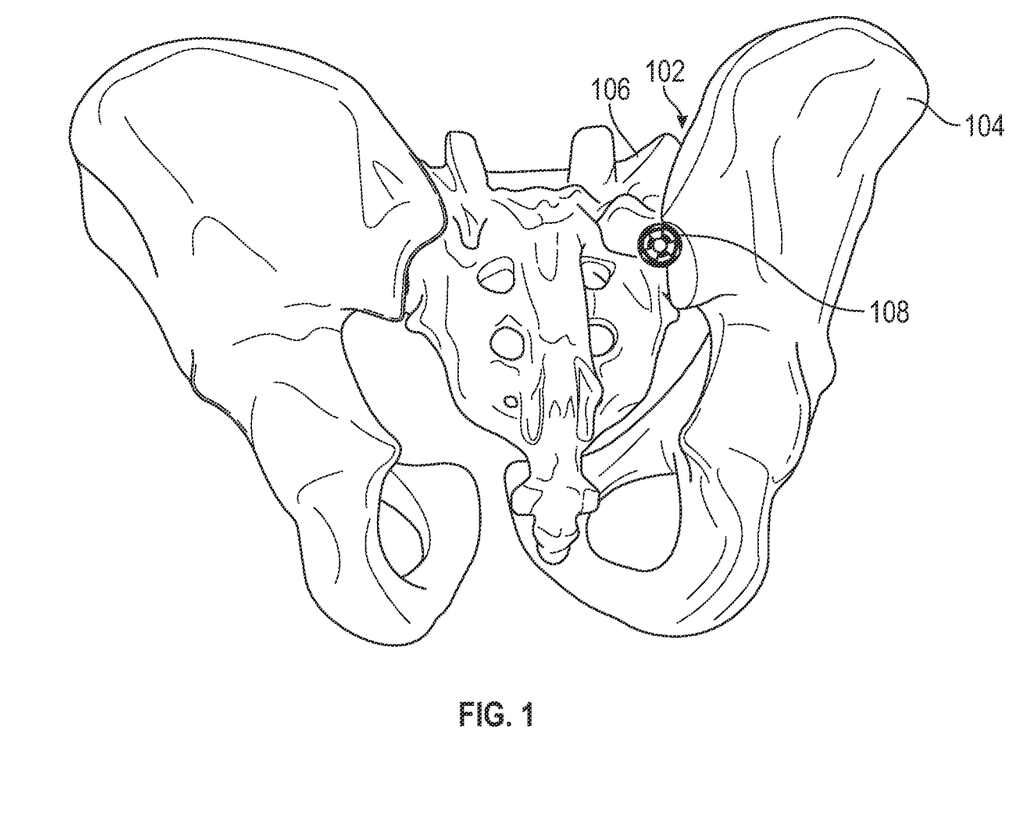
FIG. 1 illustrates an implant inserted in the sacroiliac joint for some embodiments.

Embodiments of the present disclosure are generally directed to systems, devices, and methods for stabilization and fusion of bones and/or joints, such as the sacroiliac (SI) joint 102, as shown in FIG. 1 depicting a perspective, posterior view of SI joint 102. The SI joint 102 is located between the ilium 104 and the sacrum 106 in the pelvic region of the body. An implant 108 may be inserted posteriorly into the SI joint 102 and wedged between the ilium 104 and the sacrum 106. The implant 108 may be placed in or proximal to the 51 vertebra of the sacrum 106. The implant 108 may be externally threaded, and the threads may help anchor implant 108 to ilium 104 and sacrum 106 on either side of SI joint 102.

The implant 108 may be inserted via a minimally invasive incision. A minimally invasive incision may comprise an incision of less than about 2 inches, in contrast to traditional open surgeries having five-to-six-inch incisions. Minimally invasive surgeries allow for muscle to be distracted as opposed to cut away as in open surgeries, which allows for quicker recoveries, reduced blood loss, and hospital stay, among other benefits.

The implant 108 may have a distal end configured to self-drill the implant 108 into bone, which may obviate the need to drill a pilot hole. A central section may extend proximally from the distal section and may have a lattice structure therein. A proximal section (shown in FIG. 1) may extend proximally from the central section and may be configured to receive an insertion tool for inserting implant 108 into the patient. The lattice structure may delineate the central section from the proximal and distal sections. The implant 108 may be cannulated along a length thereof. The open architecture provided by the cannula and the lattice structure may promote bone ingrowth (osseointegration) when implant 108 is implanted. Improving bone ingrowth may improve bony fusion, thereby increasing the stabilization of the bone. In contrast, typical posterior SI joint implants are solid structures that cannot be packed internally with bone graft and, as such, the bone ingrowth of such implants may be less than implant 108 described herein. The implant 108 may be formed from a metal or metal alloy, such as stainless steel or a titanium alloy. In some embodiments, the implant 108 may be formed from magnesium, a polymer, a bioresorbable material, or an allograft. In some embodiments, the implant 108 is formed by an additive manufacturing process, molding, machining, or any combination thereof. The implant 108 may also be coated with hydroxyapatite to promote bony fixation.

Implant

FIGS. 2A-2E illustrate various views of implant 108 for some embodiments of the present disclosure. Looking first at FIGS. 2A and 2B, a planar view and a cross-sectional view taken along the line A-A, respectively, are illustrated for some embodiments of the present disclosure.

Figure 2A:
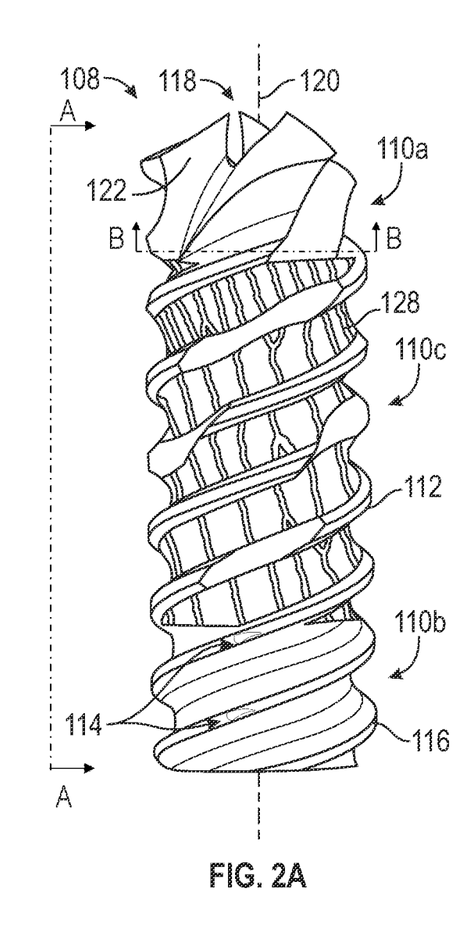
FIG. 2A illustrates a planar view of the implant for some embodiments.
Figure 2B:
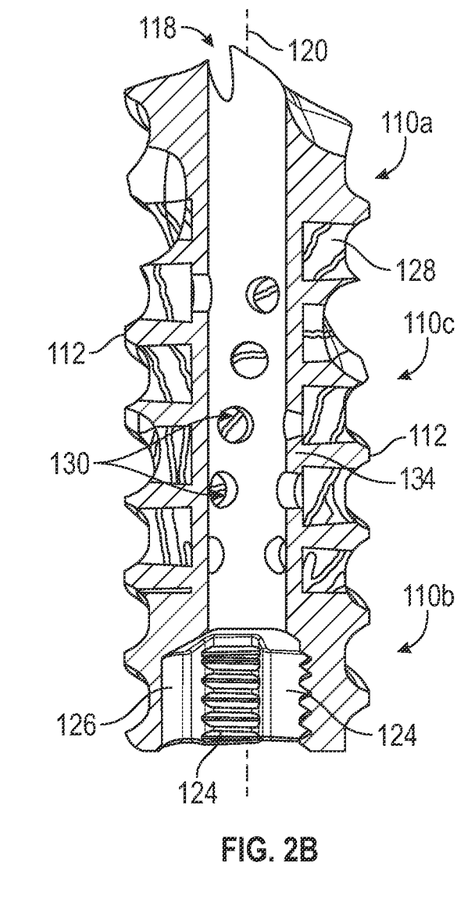
FIG. 2B illustrates a first cross-sectional view of the implant for some embodiments.

As shown, implant 108 may comprise a distal section 110a, a proximal section 110b, and a central section 110c extending between distal section 110a and proximal section 110b. Implant 108 may comprise external threads 112 along a length thereof. In some embodiments, threads 112 extend entirely along implant 108. It is contemplated that a portion of implant 108 may be unthreaded. For example, proximal section 110b may be unthreaded. As described above, when inserted in SI joint 102, threads 112 may engage with ilium 104 and sacrum 106 to maintain the position of implant 108 within SI joint 102. The threaded engagement may reduce movement of implant 108 when inserted into SI joint 102.

In some embodiments, the major diameter of threads 112 increases from distal section 110a to proximal section 110b. Providing a larger diameter at proximal section 110b may provide implant 108 with a tighter fit when inserted into the final position, which may reduce the likelihood that the implant 108 moves once inserted. In some embodiments, the major diameter of threads 112 at distal section 110a is about 7 mm, and the major diameter of threads 112 at proximal section 110b is about 10 mm. In some embodiments, the threads 112 on distal section 110a may taper down towards the distal end of distal section 110a.

Threads 112 may be single lead threads, dual lead threads, tri-lead threads, quad lead threads, or any other thread type. Threads 112 may have a major diameter of about 7 mm to about 10 mm and a minor diameter of about 5 mm to about 8 mm in some embodiments. Generally, any thread dimensions may be employed, and it will be appreciated that the thread dimensions and other dimensions of implant 108 may vary based on where in the body implant 108 is configured to be inserted. For example, an implant 108 configured for insertion into SI joint 102 may have different thread dimensions than an implant 108 configured for insertion into the foot.

Figure 2C:
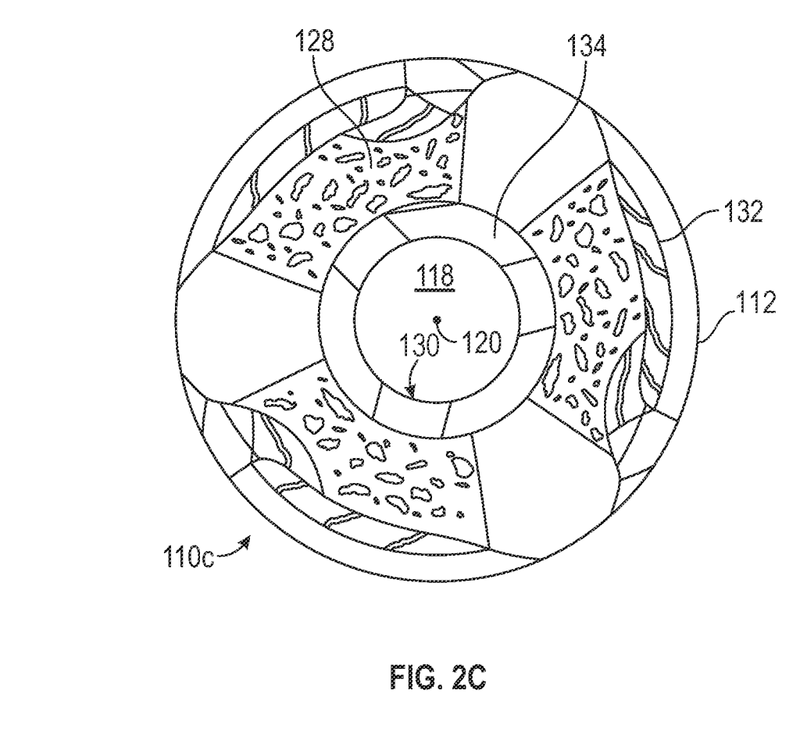
FIG. 2C illustrates a second cross-sectional view of the implant for some embodiments.
Figure 2D:
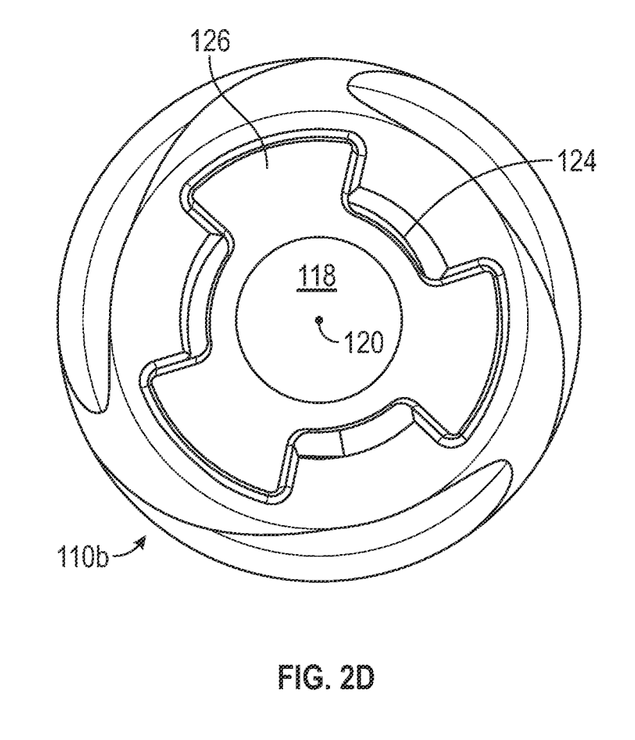
FIG. 2D illustrates a distal-looking view of the implant for some embodiments.
Figure 2E:
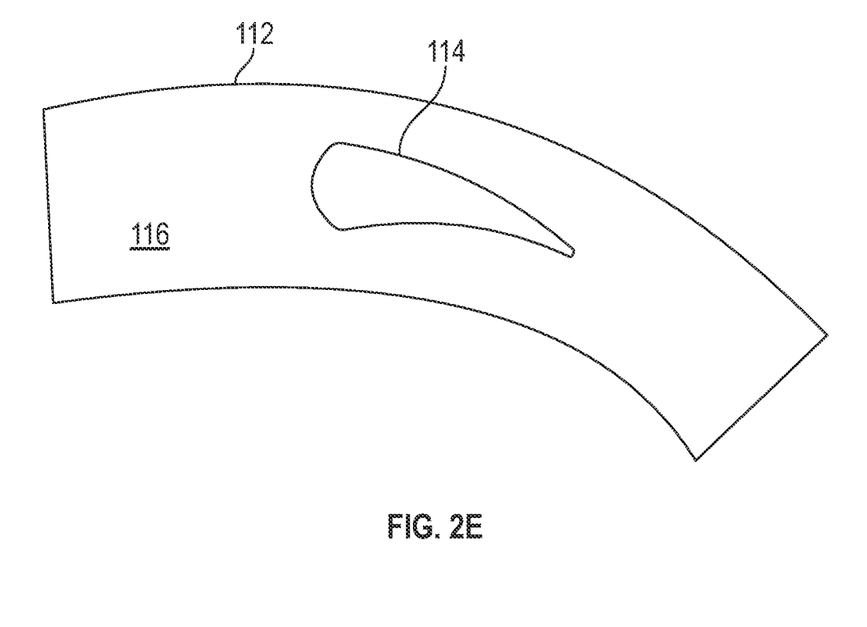
FIG. 2E illustrates a top-down view of a thread heel on a thread of the implant for some embodiments.

In some embodiments, and as shown in FIGS. 2A and 2E, threads 112 comprise heels 114 on an outer surface 116 of threads 112. The heels 114 (also referred to as hooks or teeth) may be a gripping feature configured to maintain the position/minimize movement of implant 108 in SI joint 102. When implant 108 is inserted into SI joint 102, heels 114 may at least partially embed into ilium 104 and sacrum 106 and resist movement of implant 108. Accordingly, back out of implant 108 from SI joint 102 may be mitigated.

As shown, heels 114 may be oriented in one direction. That is, heels may have a first end with a smaller width than a second end. For example, heels 114 may have a first end formed as a pointed tip and a second end formed as a blunt tip. The first end may be distal from the second end. Providing heels 114 with such a geometry may allow for heels 114 to not interfere (e.g., not resist) the threading of implant 108 into SI joint 102 while resisting any proximal motion of implant 108 out of SI joint 102. In some embodiments, heels 114 protrude from outer surface 116. In some embodiments, heels 114 protrude a height of about 1 mm above outer surface 116. In some embodiments, the height of heels 114 decreases from the second, wider end to the first, thinner end, or vice versa. In some embodiments, heels 114 are evenly spaced on threads 112 along the length of implant 108. In some embodiments, heels 114 are spaced along threads 112 by 15 degrees, 30 degrees, 45 degrees, 90 degrees, 180 degrees, or in any other increment. In some embodiments, the spacing between heels 114 is not even. For example, it may be advantageous to have more heels 114 and/or reduced spacing between heels 114 near proximal section 110b than near distal section 110a to aid in mitigating back out of implant 108. Generally, any number, arrangement, sizing, spacing, or any combination thereof of heels 114 on threads 112 is within the scope of the present disclosure.

In some embodiments, implant 108 has a cannula 118 extending along a length thereof. The cannula 118 may extend entirely through implant 108. In some embodiments, implant 108 may be symmetrical about a longitudinal axis 120, and cannula 118 may extend along longitudinal axis 120 such that cannula 118 presents a central bore through implant 108. In some embodiments, cannula 118 is sized to receive a guidewire therethrough such that implant 108 may be inserted over the guidewire. As shown in FIG. 2B, cannula 118 may have a variable diameter. For example, proximal section 110b may have a larger diameter to accommodate an insertion instrument (discussed below). In some embodiments, cannula 118 does not extend entirely through implant 108 such that distal section 110a is closed. In some embodiments, implant 108 does not comprise a cannula 118, presenting a solid structure. In some such embodiments, proximal section 110b may be formed with a recess as shown for coupling to an insertion instrument.

As discussed previously, distal section 110a may be configured for self-drilling implant 108 into bone such that a pilot hole may not need to be drilled into the patient. In some embodiments, distal section 110a comprises one or more flutes 122 that aid in self-drilling. Additionally, threads 112 may be sharp to aid in self-drilling. For example, threads 112 may be cutting threads or box threads configured to cut through bone. Threads 112 and/or flutes 122 may also self-harvest the drilled bone, which may further promote bone ingrowth of implant 108.

Looking now at FIGS. 2B and 2D, it can be seen that proximal section 110b may be configured for coupling to the insertion instrument. In some embodiments, proximal section 110b may comprise internal threads 124 and recesses 126. In some embodiments, each recess 126 mates with a corresponding prong of the insertion instrument, and internal threads 124 couple to a threaded rod of the insertion instrument. Accordingly, once coupled, the insertion instrument may be used to insert implant 108 into SI joint 102. When implant 108 is formed without a cannula 118, proximal section 110b may still comprise internal threads 124 and recesses 126, while distal section 110a and central section 110c may be solid through their center.

As shown in FIGS. 2A-2C, central section 110c may comprise a lattice structure 128 and openings 130 (also referred to as fenestrations). The portion of implant 108 that is distal from lattice structure 128 may be distal section 110a, and the portion of implant 108 that is proximal from 122 may be proximal section 110b. Providing a lattice structure 128 may reduce the overall weight of implant 108. Furthermore, the lattice structure 128 provides for open volume in which bone graft may flow to promote bone ingrowth. In some embodiments, implant 108 may be pre-packed and/or post-packed with bone graft to promote bony fusion. Openings 130 may fluidly connect cannula 118 to lattice structure 128, thereby allowing for bone graft to be packed via cannula 118 and travel into lattice structure 128. Openings 130 may follow the thread path of threads 112. By following the thread path of threads 112, bone ingrowth may be enabled across or through implant 108 from ilium 104 to sacrum 106. In some embodiments, openings 130 are arranged linearly in central section 110c. Generally, any arrangement of openings 130 within central section 110c is within the scope hereof. In some embodiments, central section 110c comprises a length of about 20% to about 80% of an overall length of implant 108. In some embodiments, central section 110c comprises a length of about 30% to about 60% of an overall length of implant 108. In some embodiments, central section 110c comprises a length of about 50% of an overall length of implant 108. In some embodiments, implant 108 comprises a length measured from proximal section 110b to distal section 110a of about 25 mm to about 35 mm.

Referring now to FIG. 2C, a cross-sectional, proximal-looking view taken along the lines B-B shown in FIG. 2A is illustrated for some embodiments. As shown, lattice structure 128 extends laterally substantially from a minor diameter 132 of threads 112 to a core region 134 of implant 108. The core region 134 may be an interior region of implant 108 through which lattice structure 128 does not extend. Core region 134 may be adjacent to cannula 118. Core region 134 may be generally solid; however, and as shown, openings 130 may extend through portions of core region 134 to fluidly connect cannula 118 to lattice structure 128.

Accordingly, bone graft may be inserted into cannula 118 and flow into lattice structure 128 via openings 130. Furthermore, as seen best in FIG. 2B, the core region 134 is mechanically connected to the solid thread profile at various locations along the length of central section 110c, which improves the mechanical strength of implant 108 as compared to an implant in which lattice structure 128 was adjacent to cannula 118 (i.e., if core region 134 was not present).

As previously discussed, implant 108 may be additively manufactured. Accordingly, lattice structure 128 may be a software-generated lattice structure printed by an additive manufacturing device. In some embodiments, lattice structure 128 is a triply periodic minimal surface (TPMS) lattice. In some embodiments, lattice structure 128 is a split-P TPMS lattice, or may be any other TPMS lattice type. In some embodiments, lattice structure 128 is one of a cubic lattice, a pentagonal lattice, a hexagonal lattice, an octagonal lattice, or the like. Generally, any type of lattice structure may be used. The lattice structure 128 may be roughened, which may further promote bone ingrowth of implant 108. Further, lattice structure 128 may comprise more than one lattice type. For example, a first portion of lattice structure 128 may have a first lattice type and a second portion of lattice structure 128 may have a second lattice type. It is contemplated that the lattice structure may be selected and/or customized based on the specific anatomy of the patient.

In some embodiments, implant 108 is formed from a metal or metal alloy. In some embodiments, implant 108 is formed from a titanium or titanium alloy. In some embodiments, implant 108 comprises Ti-6Al-4V, which is an alpha-beta titanium alloy that provides a high specific strength and good corrosion resistance. It is contemplated that other alpha-beta titanium alloys may be used without departing from the scope hereof. For example, implant 108 may comprise TI-6Al-7Nb. Other metal and metal alloys may be used such as, but not limited to, cobalt chrome, stainless steel, nitinol, or tantalum. In some embodiments, implant 108 is formed from a polymer, such as PEEK. In some embodiments, implant 108 is formed from a bioresorbable material such as a ceramic, hydroxyapatite, or magnesium.

In some embodiments, implant 108 is post-processed after printing via hot isostatic pressing. Other post-processing steps, such as heat treatment, machining, surface treatments (e.g., roughening), and the like may be performed. For example, in some embodiments, at least a portion of implant 108 may undergo a roughening treatment. Providing a roughened surface may promote bone ingrowth of implant 108.

Insertion Instrument and Surgical Tools

Figure 3A:
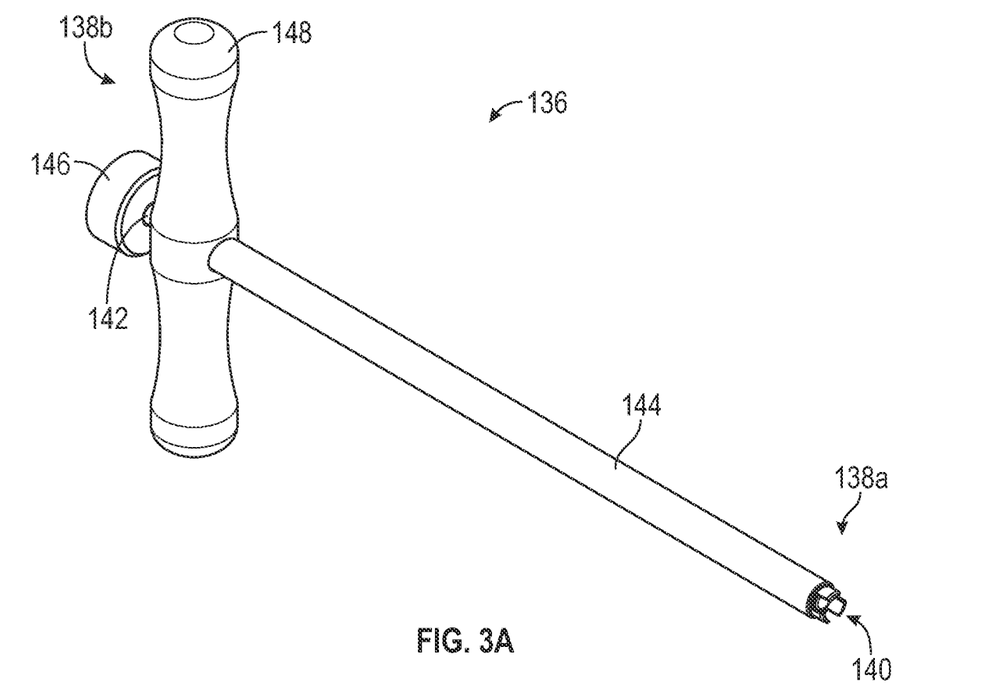
FIG. 3A illustrates a perspective view of an insertion instrument for some embodiments.
Figure 3B:
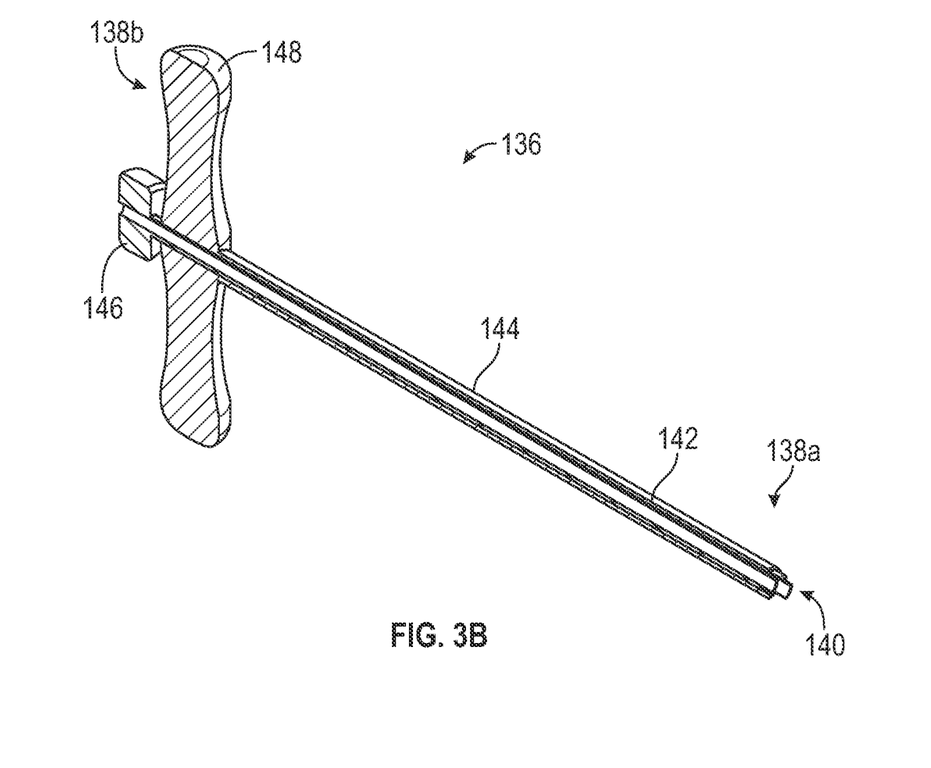
FIG. 3B illustrates a cross-sectional view of the insertion instrument for some embodiments.
Figure 3C:
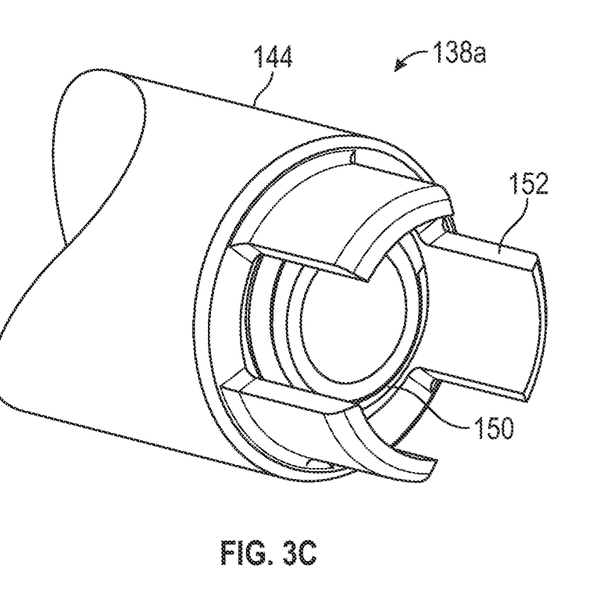
FIG. 3C illustrates a close-up view of a distal end of the insertion instrument for some embodiments.

FIGS. 3A and 3B illustrate a perspective view and a cross-sectional view, respectively, of an insertion instrument 136 for some embodiments of the present disclosure. FIG. 3C illustrates a close-up view of a distal end of the insertion instrument 136 for some embodiments. Once the SI joint 102 is prepared for insertion of implant 108 (discussed further below), insertion instrument 136 may be used to insert implant 108 into SI joint 102.

Insertion instrument 136 may comprise a distal end 138a for coupling to implant 108 and a proximal end 138b for the operator to interface with insertion instrument 136. A bore 140 may extend lengthwise through insertion instrument 136. The bore 140 may provide a path for inserting insertion instrument 136 over a guidewire (FIG. 4) during the insertion process, as discussed further below.

Insertion instrument 136 may further comprise a rod 142 that may be received within a shaft 144. Rod 142 and shaft 144 may be concentric. An inner surface of shaft 144 may abut an outer surface of rod 142. A rod handle 146 may be coupled to a proximal end of the rod 142, and a shaft handle 148 may be coupled to the shaft 144. Shaft handle 148 may comprise a bore through which shaft 144 may extend such that a portion of shaft 144 extends proximally from shaft handle 148. In some embodiments, a proximal face of shaft handle 148 coincides with a proximal face of shaft 144. In some embodiments, rod 142 is movable longitudinally within shaft 144. The travel distance of rod 142 in the distal direction may be limited by a proximal face of shaft handle 148.

As shown in FIG. 3C, a distal end of rod 142 may comprise external threads 150 configured to threadedly engage with internal threads 124 on proximal section 110b. A distal end of shaft 144 may comprise prongs 152 configured to engage with recesses 126 in proximal section 110b. An operator may rotate rod handle 146 to mate external threads 150 with internal threads 124. Once engaged, prongs 152 may be inserted into recesses 126 to complete the coupling of insertion instrument 136 with implant 108. When implant 108 is coupled to insertion instrument 136, the operator may use shaft handle 148 to rotate insertion instrument 136, thereby driving implant 108 into SI joint 102. The flutes 122 and/or threads 112 may self-drill implant 108 into SI joint 102.

In some embodiments, insertion instrument 136 comprises titanium or a titanium alloy. In some embodiments, insertion instrument 136 comprises stainless steel. In some embodiments, insertion instrument 136 comprises a polymer, a plastic, a bioabsorbable material, or any combination thereof. For example, insertion instrument insertion instrument 136 may be formed from polyacrylamide or IXEF®. In some embodiments, insertion instrument 136 is additively manufactured and may be formed from RULON, PEEK, or the like. In some embodiments, at least a portion of insertion instrument 136 is radiopaque or radiolucent. In some embodiments, insertion instrument 136 is disposable.

In some embodiments, one or more components of insertion instrument 136 are coated in a biocompatible, corrosion resistant material to help protect and/or strengthen the component. For example, some or all portions of insertion instrument 136 may be advantageously reinforced with a coating material to increase the durability of the components while maintaining safety to the patient by the coating material being of a biocompatible substance. Such a coating material may be applied specifically to components of insertion instrument 136 that come into contact with tissue of the patient. In some embodiments, the coating material may be an anodized metal. In some embodiments, the coating material may be formed by an electroplating process, such as a hard chromium electroplating process. For example, in some embodiments, the coating material may be MEDCOAT 2000™. In some embodiments, the thickness of the coating material may be between about 1 μm to about 15 μm. In some embodiments, the coating material may be between about 2 μm to about 10 μm.

Figure 4:
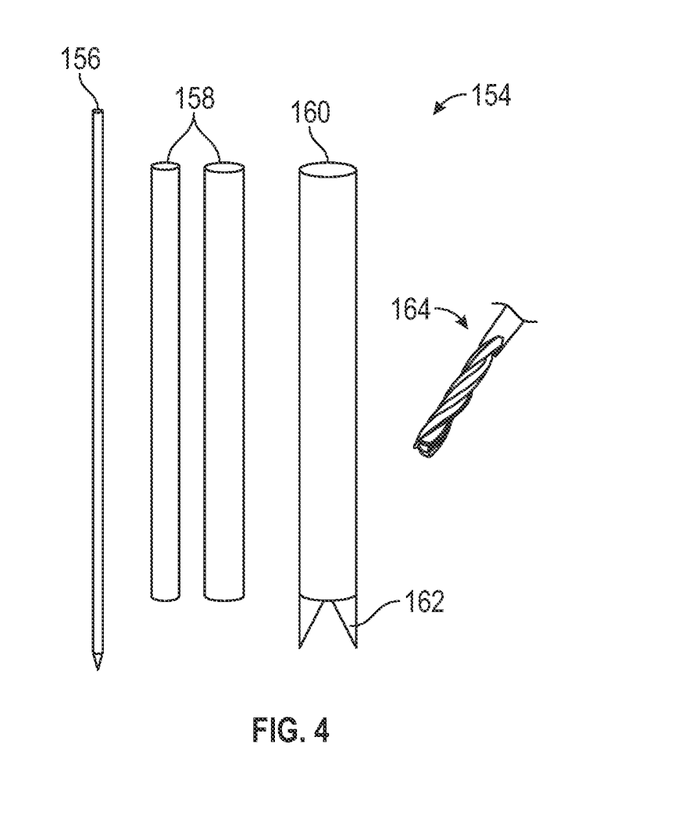
FIG. 4 illustrates exemplary tools for a surgical kit for inserting the implant and preparing a target insertion space for insertion for some embodiments.

Turning now to FIG. 4, an exemplary set of tools 154 is illustrated for preparing a target space (e.g., SI joint 102) for insertion of an implant 108 for some embodiments of the present disclosure. In some embodiments, one or more of exemplary tools 154 may be provided as part of a surgical kit along with implant 108 and/or insertion instrument 136 for bony fixation of a target space, such as SI joint 102.

In some embodiments, tools 154 comprises a guidewire 156. Guidewire 156 may be inserted into a minimally invasive incision and, under fluoroscopy, guidewire 156 may be advanced to locate the target space where it is desired to place implant 108. In some embodiments, tools 154 comprises one or more dilators 158. Dilators 158 may be hollow tubes that are placed over guidewire 156 to create a working channel for insertion of implant 108. Dilators 158 may be provided in increasing sizes such that a larger sized dilator 158 may be placed over a smaller-sized dilator to dilate the target space.

In some embodiments, tools 154 comprises a final dilator 160. The final dilator may have a larger size than dilators 158 such that final dilator 160 may be placed over the largest dilator 158. Additionally, in some embodiments, the final dilator 160 may have one or more tangs 162. The tangs 162 may be configured to dock into the SI joint 102. For example, a first tang 162 may engage with the ilium 104 and a second tang 162 may engage with the sacrum 106. Docking one or more tangs 162 with ilium 104 and/or sacrum 106 may provide positive feedback to the surgeon to indicate that SI joint 102 was correctly located. Final dilator 160 may also provide further distraction to SI joint 102 to prepare SI joint 102 for implantation of implant 108. Through final dilator 160, implant 108 and insertion instrument 136 may be inserted when implanting implant 108. In some embodiments, final dilator 160 comprises at least one tang 162. In some embodiments, final dilator 160 comprises two or more tangs 162. In some embodiments, tangs 162 are wedge shaped. Other shapes are within the scope hereof. Generally, final dilator 160 may have a distal end that is configured for engaging with bone such that final dilator 160 can dock into the target space. Providing a final dilator 160 as discussed herein may be advantageous in correctly locating SI joint 102, which may be difficult from a posterior approach due to the irregular shape of the joint that makes the joint difficult to view under fluoroscopy. Accordingly, with the positive feedback provided by final dilator 160, the surgeon may be assured that the correct location for inserting implant 108 has been located.

In some embodiments, tools 154 comprises a drill bit 164. Drill bit 164 may be used for drilling a pilot hole to access the target space. In some embodiments, drill bit 164 is cannulated, as shown, such that drill bit 164 may be inserted over guidewire 156. In some embodiments, tools 154 further comprises a decorticator (not shown) for roughening the target space. The decorticator may likewise be cannulated for insertion over guidewire 156. It will be appreciated that various other tools may be provided with a surgical kit for bony fusion without departing from the scope hereof. For example, in some embodiments, implant 108 may be used with a bone plate through which one or more implants 108 may be inserted for bony fusion.

Implant Insertion Method

Figure 5:
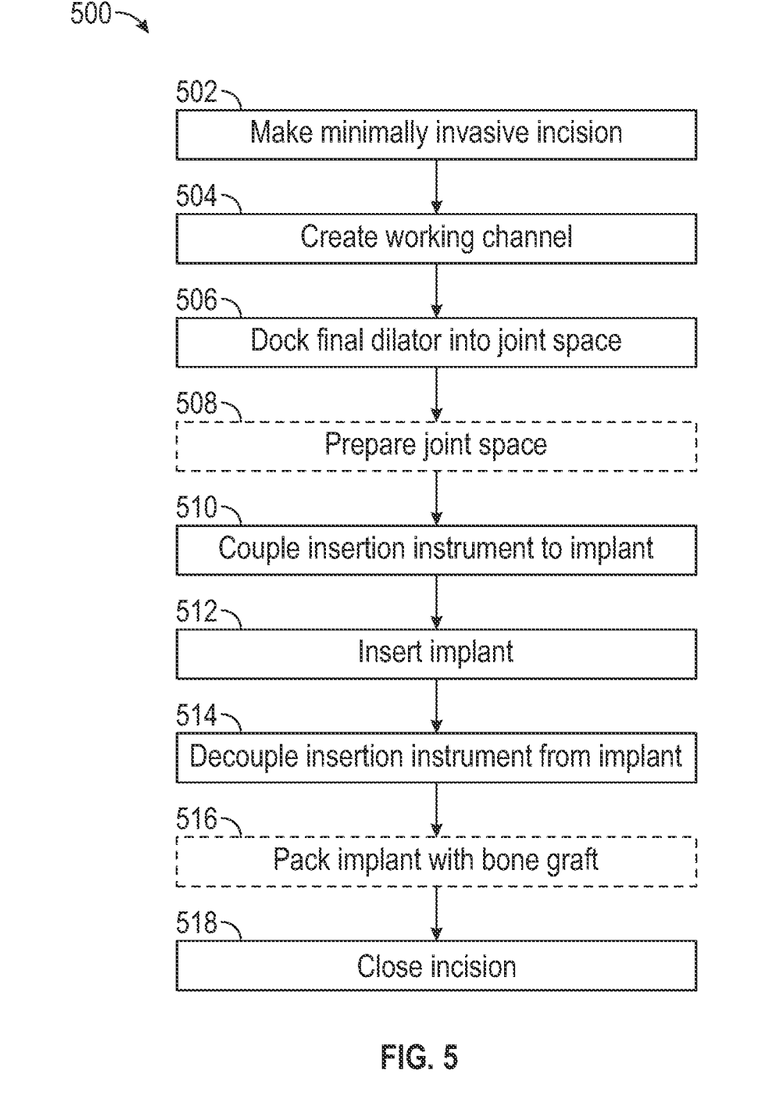
FIG. 5 illustrates an operational method for inserting the implant for some embodiments.

FIG. 5 illustrates a method 500 for inserting implant 108 into SI joint 102 in accordance with embodiments of the present disclosure. One or more implants 108 may be inserted into the SI joint 102 to provide fusion and stabilization thereof. In some embodiments, the implant 108 is inserted at the 51 level of the spine. Placement of the implants implant 108 may be done to avoid damaging the neuroforamen that are medial from the sacrum 106. While method 500 is discussed with respect to a posterior approach, one of skill in the art will appreciate that method 500 may be suitably modified to insert implant 108 via other approaches, such as anteriorly.

Method 500 may begin at step 502 where a minimally invasive incision may be made on the patient. As described above, minimally invasive incisions reduce blood loss, recovery time, and hospital stay, among other benefits, as compared to open surgery. However, it is contemplated that embodiments herein may be practiced in an open surgery without departing from the scope hereof. In some embodiments, the minimally invasive incision is made to provide posterior access to SI joint 102 such that implant 108 may be inserted into SI joint 102 via a posterior approach as discussed with respect to FIG. 1. The patient may be placed in a prone position to provide posterior access to SI joint 102. In some embodiments, a separate incision is made for each implant 108 inserted into the SI joint 102. In some embodiments, a single incision is made for inserting implant 108 into SI joint 102. In some embodiments, one, two, three or more implants 108 may be inserted into SI joint 102.

Next, at step 504, a working channel for inserting the implant 108 may be created. In some embodiments, the working channel is created by successively inserting one or more dilators 158 over a guidewire 156 that is inserted into SI joint 102 to dilate soft tissues surrounding SI joint 102. In embodiments where multiple implants 108 are inserted, a parallel pin guidewire tool may be used to insert a guidewire 156 for each implant 108. The guidewires 156 may be inserted by tapping or any other method as will be appreciated by one of skill in the art.

Thereafter, at step 506, final dilator 160 may be inserted. The final dilator 160 may comprise tangs, prongs, or other engaging features that may dock into SI joint 102. The dilators 158, 160 may be tubes or other hollow bodies that provide a pathway for inserting implant 108 and insertion instrument 136 therein to access SI joint 102.

At optional step 508, one or more site preparation steps may be taken to prepare SI joint 102 for insertion of implant 108. In some embodiments, SI joint 102 may be roughened using a cannulated decorticator or other like tool. Another preparation step may comprise drilling a pilot hole to access SI joint 102, which may be done using drill bit 164. As described above, distal section 110a may be configured to self-drill implant 108 into SI joint 102 such that drilling a pilot hole may be unnecessary.

Next, at step 510, with SI joint 102 prepared for insertion of implant 108, implant 108 may be coupled to insertion instrument 136. As described above, external threads 150 on rod 142 may couple to internal threads 124 in proximal section 110b and prongs 152 on shaft 144 may couple to recesses 126 in proximal section 110b. Threadedly engaging external threads 150 with internal threads 124 may lock implant 108 to insertion instrument 136, while the engagement between prongs 152 and recesses 126 may allow for the rotational movement of insertion instrument 136 to rotate implant 108.

Next, at step 512, implant 108 may be inserted into SI joint 102 by rotationally driving insertion instrument 136 via shaft handle 148. As implant 108 is advanced distally, flutes 122 and/or threads 112 may work to self-drill implant 108 into SI joint 102. As discussed above, the procedure may be conducted under fluoroscopy such that the surgeon may monitor the position of implant 108 during insertion. When in the final position, threads 112 may be engaged with ilium 104 and sacrum 106, and this threaded engagement may mitigate movement of implant 108 once implanted.

Furthermore, heels 114 may engage with ilium 104 and sacrum 106 to prevent backing out of implant 108 from SI joint 102. The final position of the implant 108 may be from the posterior-inferior aspect of the articular portion of the joint 102, anterior to the posterior superior iliac spine (PSIS), and posterior to the posterior inferior iliac spine (PIIS), ranging from 0 to 10 mm from the proximal end of SI joint 102.

Thereafter, at step 514, insertion instrument 136 may be decoupled from implant 108. Decoupling insertion instrument 136 from implant 108 may comprise unthreading external threads 150 from internal threads 124 and pulling insertion instrument 136 proximally to disengage prongs 152 from recesses 126.

Next, at optional step 516, implant 108 may be packed with bone graft. The bone graft may be autograft, allograft, a synthetic bone graft, or the like. Bone graft may be inserted via cannula 118 and flow through openings 130 and into lattice structure 128. Because insertion instrument 136 is also cannulated, the bone graft may be inserted through bore 140 and into cannula 118 when insertion instrument 136 is coupled to implant 108. As described above, the open architecture of implant 108 may improve bone ingrowth because the bone graft may flow within the openings of implant 108. Accordingly, more bone graft may be added to implant 108 than prior implants. Implant 108 may also have bone graft packed to the exterior thereof. Lastly, at step 518, the incision may be closed to complete the insertion process.

While method 500 is discussed with respect to inserting implant 108 into SI joint 102, it will be appreciated that method 500 may be suitably modified for insertion of implant 108 at other locations in the body, such as the foot, ankle, shoulder, face, etc. For these operations, a posterior approach may not be taken, and embodiments of the present disclosure should not be construed as limited to only posterior approaches. Generally, a method for inserting implant 108 may comprise: (1) providing access to the target space (e.g., via an incision and subsequent dilations, etc.); (2) coupling implant 108 to insertion instrument 136; (3) inserting implant 108 with insertion instrument 136; and (4) performing any post-insertion steps (e.g., post-packing, etc.).

In some embodiments, the above-described method 500 may be provided as instructions with a surgical kit. For example, the surgical kit may comprise the instrumentation required to perform the surgery, such as one or more implants 108, insertion instrument 136, and tools 154. The surgical kit may provide multiple sizes of the tools, implants 108, and inserter instruments 136, which may be selected based on the size of the patient. The surgeon may use the surgical kit to perform the fusions and follow the above-described method to carry out the operations.

Exemplary Implantation Sites

Figure 6A:
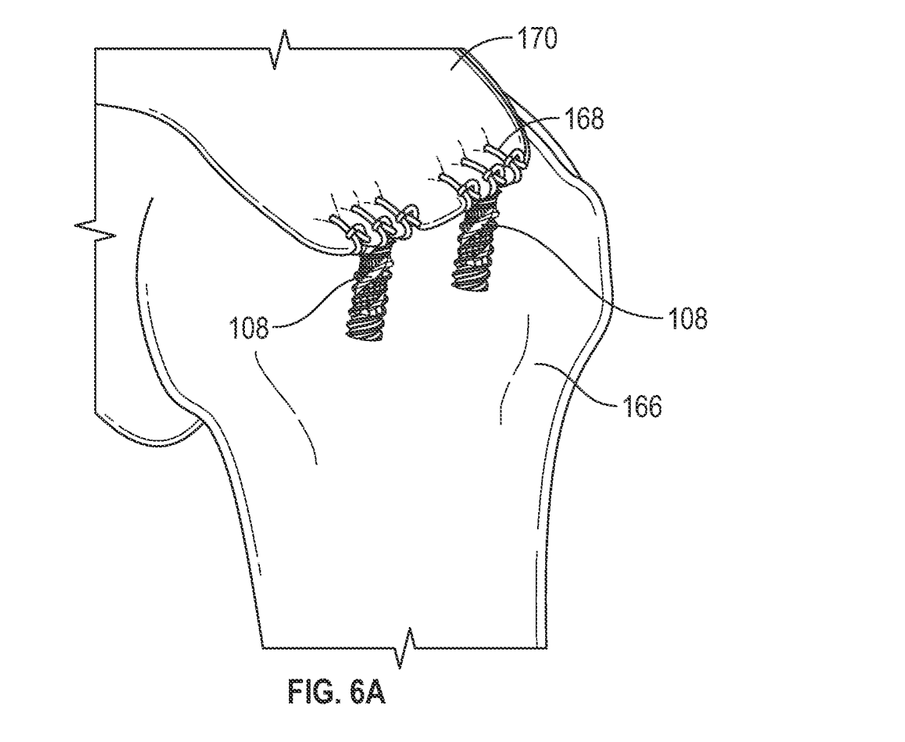
FIG. 6A illustrates an exemplary embodiment of the implant inserted in the rotator cuff for some embodiments.
Figure 6B:
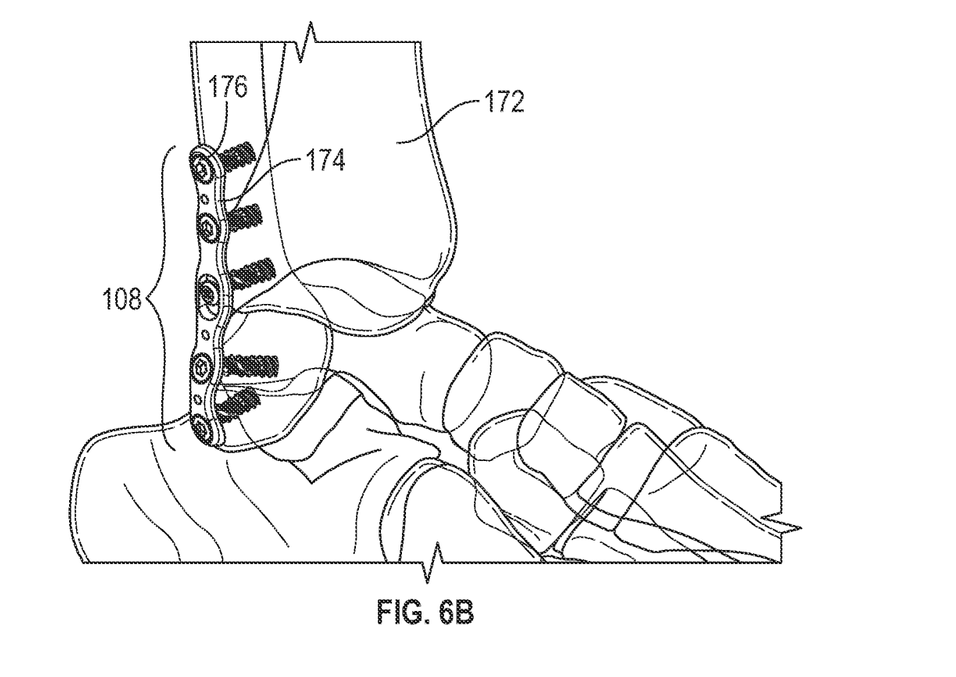
FIG. 6B illustrates an exemplary embodiment of the implant inserted in the ankle for some embodiments.

FIGS. 6A and 6B illustrate exemplary use cases of implant 108 in other regions of the body in accordance with embodiments of the present disclosure. Looking first at FIG. 6A, implant 108 is shown for use in repairing a rotator cuff for some embodiments. Here, implant 108 may function as an anchor commonly used in rotator cuff repair. One or more implants 108 may be placed into the humerus 166. Implant 108 may be configured with suture strands 168 that can be passed through the tendon 170 as will be appreciated by one of skill in the art. The open architecture of implant 108, along with additively manufacturing implant 108 from a titanium alloy, may be advantageous over prior anchors.

Looking now at FIG. 6B, implant 108 is depicted inserted into an ankle 172 for some embodiments of the present disclosure. As shown, a plurality of implants 108 are inserted through a bone plate 174. Further, it is contemplated that each implant 108 may be formed with a head 176 (e.g., a screw head) for retaining implant 108 in bone plate 174.

It is contemplated that implant 108 may be used with a bone plate 174 at various regions of the body. Generally, implant 108 may be useful with any bony structure that requires fusion and/or stabilization.

(A1) An implant for bony fusion at a target space, comprising: a plurality of external threads extending along a length of the implant; a cannula extending along a longitudinal axis of the implant; a distal section; a proximal section configured to be coupled to an insertion instrument; and a central section between the proximal section and the distal section, the central section comprising: an interior core region adjacent to the cannula; a lattice structure located laterally between the interior core region and a minor diameter of the plurality of external threads; and a plurality of openings extending through the interior core region, the plurality of openings connecting the lattice structure to the cannula.

(A2) For the implant denoted as (A2), wherein the implant is configured to be packed with bone graft, and wherein the plurality of openings is connected to the lattice structure such that the bone graft flows between the plurality of openings and the lattice structure.

(A3) For the implant denoted as (A1) or (A2), wherein the distal section comprises at least one cutting flute for self-drilling the implant into the target space.

(A4) For the implant denoted as any of (A1) through (A3), wherein the proximal section comprises internal threading for threadedly engaging the insertion instrument, wherein rotation of the insertion instrument rotates the implant for insertion into the target space.

(A5) For the implant denoted as any of (A1) through (A4), wherein at least a portion of the plurality of external threads comprises at least one thread heel configured to reduce proximal movement of the implant when inserted into the target space.

(A6) For the implant denoted as any of (A1) through (A5), wherein the at least one thread heel is oriented in a first direction to prevent interference with threading of the implant during insertion.

(A7) For the implant denoted as any (A1) through (A6), wherein the central section comprises a length of about 30% to about 60% of the length of the implant.

(A8) For the implant denoted as any of (A1) through (A7), wherein the implant is formed from at least one of: a titanium alloy, stainless steel, magnesium, a polymer, a bioresorbable material, or an allograft, and wherein the implant is coated with hydroxyapatite.

(B1) An implant for bony fusion of a target space, comprising: a cannula along a longitudinal axis of the implant; a distal section configured to self-drill the implant into bone; a proximal section; and a central section between the distal section and the proximal section, comprising: a lattice structure fluidly connected to the cannula, wherein the lattice structure is configured to receive bone graft for bone ingrowth of the implant, wherein the implant comprises a plurality of external threads extending along a length of the implant.

(B2) For the implant denoted as (B1), wherein the central section further comprises: a core region adjacent to the cannula, and a plurality of fenestrations extending through the core region to fluidly connect the cannula to the lattice structure.

(B3) For the implant denoted as (B1) or (B2), wherein the lattice structure extends laterally from a perimeter of the core region to a minor diameter of the plurality of external threads.

(B4) For the implant denoted as any of (B1) through (B3), wherein the plurality of fenestrations follows a thread path of the plurality of external threads.

(B5) For the implant denoted as any of (B1) through (B4), wherein the implant comprises a variable diameter that increases from the distal section to the proximal section.

(B6) For the implant denoted as any of (B1) through (B5), wherein the target space is a sacroiliac joint, and wherein the plurality of external threads of the implant is configured to embed into a sacrum and an ilium of the sacroiliac joint.

(B7) For the implant denoted as any of (B1) through (B6), wherein the implant is configured to be inserted into the sacroiliac joint via a posterior approach.

(B8) For the implant denoted as any of (B1) through (B7), wherein the distal section comprises a plurality of internal threads and a plurality of recesses configured for coupling to an insertion instrument.

(C1) A method for bony fusion of a target space, comprising: providing an implant having a cannula along a longitudinal axis, comprising: a plurality of external threads extending along a length of the implant; a distal section; a proximal section configured to be coupled to an insertion instrument; and a central section between the proximal section and the distal section, the central section comprising: an interior core region adjacent to the cannula; a lattice structure located laterally between the interior core region and a minor diameter of the plurality of external threads; and a plurality of openings extending through the interior core region, the plurality of openings connecting the lattice structure to the cannula; and providing instructions, the instructions comprising steps of: couple the implant to the insertion instrument; and insert the implant into the target space using the insertion instrument.

(C2) For the method denoted as (C1), wherein the instructions further comprise: make a minimally invasive incision; successively insert a series of dilators into the minimally invasive incision to create a working channel; and dock into the target space using a final dilator, the final dilator comprising at least one distal tang to engage with the target space.

(C3) For the method denoted as (C1) or (C2), wherein the distal section comprises cutting threads and flutes configured to self-drill the implant into the target space.

(C4) For the method denoted as any of (C1) through (C3), wherein the instructions further comprise: pack the implant with bone graft, wherein the bone graft flows from between the cannula, the plurality of openings, and the lattice structure.

Many different arrangements of the various components depicted, as well as components not shown, are possible without departing from the scope of the claims below. Embodiments of the present disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims. Although the present disclosure has been described with reference to the embodiments illustrated in the attached drawing figures, it is noted that equivalents may be employed, and substitutions made herein, without departing from the scope of the present disclosure as recited in the claims.

The invention claimed is:

1. An implant for bony fusion at a target space, comprising:
  a plurality of external threads extending along a length of the implant;
  a cannula extending along a longitudinal axis of the implant;
  a distal section;
  a proximal section configured to be coupled to an insertion instrument; and
  a central section between the proximal section and the distal section, the central section comprising:
    an interior core region adjacent to the cannula;
    a lattice structure located laterally between the interior core region and a minor diameter of the plurality of external threads; and
    a plurality of openings extending through the interior core region, the plurality of openings connecting the lattice structure to the cannula.

2. The implant of claim 1,
  wherein the implant is configured to be packed with bone graft, and
  wherein the plurality of openings is connected to the lattice structure such that the bone graft flows between the plurality of openings and the lattice structure.

3. The implant of claim 1, wherein the distal section comprises at least one cutting flute for self-drilling the implant into the target space.

4. The implant of claim 1, wherein the proximal section comprises internal threading for threadedly engaging the insertion instrument, wherein rotation of the insertion instrument rotates the implant for insertion into the target space.

5. The implant of claim 1, wherein at least a portion of the plurality of external threads comprises at least one thread heel configured to reduce proximal movement of the implant when inserted into the target space.

6. The implant of claim 5, wherein the at least one thread heel is oriented in a first direction to prevent interference with threading of the implant during insertion.

7. The implant of claim 1, wherein the central section comprises a length of about 30% to about 60% of the length of the implant.

8. The implant of claim 1, wherein the implant is formed from at least one of: a titanium alloy, stainless steel, magnesium, a polymer, a bioresorbable material, or an allograft, and wherein the implant is coated with hydroxyapatite.

9. An implant for bony fusion of a target space, comprising:
  a cannula along a longitudinal axis of the implant;
  a distal section configured to self-drill the implant into bone;
  a proximal section; and
  and a central section between the distal section and the proximal section, comprising:
  a lattice structure fluidly connected to the cannula, wherein the lattice structure is configured to receive bone graft for bone ingrowth of the implant,
  wherein the implant comprises a plurality of external threads extending along a length of the implant;
  wherein the central section further comprises: a core region adjacent to the cannula, and a plurality of fenestrations extending through the core region to fluidly connect the cannula to the lattice structure.

10. The implant of claim 9, wherein the lattice structure extends laterally from a perimeter of the core region to a minor diameter of the plurality of external threads.

11. The implant of claim 9, wherein the plurality of fenestrations follows a thread path of the plurality of external threads.

12. The implant of claim 9, wherein the implant comprises a variable diameter that increases from the distal section to the proximal section.

13. The implant of claim 9,
  wherein the target space is a sacroiliac joint, and
  wherein the plurality of external threads of the implant is configured to embed into a sacrum and an ilium of the sacroiliac joint.

14. The implant of claim 13, wherein the implant is configured to be inserted into the sacroiliac joint via a posterior approach.

15. The implant of claim 9, wherein the proximal section comprises a plurality of internal threads and a plurality of recesses configured for coupling to an insertion instrument.

16. A method for bony fusion of a target space, comprising:
  providing an implant having a cannula along a longitudinal axis, comprising:
    a plurality of external threads extending along a length of the implant;
    a distal section;
    a proximal section configured to be coupled to an insertion instrument; and
    a central section between the proximal section and the distal section, the central section comprising:
      an interior core region adjacent to the cannula;
      a lattice structure located laterally between the interior core region and a minor diameter of the plurality of external threads; and
      a plurality of openings extending through the interior core region, the plurality of openings connecting the lattice structure to the cannula; and
  providing instructions, the instructions comprising steps of:
    couple the implant to the insertion instrument; and
    insert the implant into the target space using the insertion instrument.

17. The method of claim 16, wherein the instructions further comprise:
  make a minimally invasive incision;
  successively insert a series of dilators into the minimally invasive incision to create a working channel; and
  dock into the target space using a final dilator, the final dilator comprising at least one distal tang to engage with the target space.

18. The method of claim 16, wherein the distal section comprises cutting threads and flutes configured to self-drill the implant into the target space.

19. The method of claim 16, wherein the instructions further comprise:
  pack the implant with bone graft,
  wherein the bone graft flows from between the cannula, the plurality of openings, and the lattice structure.

20. The implant of claim 9, wherein the implant is formed from at least one of: a titanium alloy, stainless steel, magnesium, a polymer, a bioresorbable material, or an allograft.

* * * * *